United States Patent [19]

Rabinovitz

[11] Patent Number: 4,755,515

[45] Date of Patent: Jul. 5, 1988

[54] CHEMOTHERAPEUTIC 1-(2-CHLOROETHYL)-4-(3-CHLOROPROPYL)-PIPERAZINE, DIHYDROCHLORIDE

[75] Inventor: Marco Rabinovitz, Bethesda, Md.

[73] Assignee: The United States of America as represented by the Department of Health and Human Services, Washington, D.C.

[21] Appl. No.: 896,262

[22] Filed: Aug. 14, 1986

[51] Int. Cl.[4] .................. A61K 31/495; C07D 295/00
[52] U.S. Cl. ..................................... 514/255; 544/358
[58] Field of Search ........................ 544/358; 514/255

[56] References Cited

PUBLICATIONS

McNair et al, CA 62-3289 (1965).
Ishidate et al, CA 50-5776 (1956).
Sakurai et al, CA 49-11091 (1955).
Aiko, CA 49-11962 (1955).
Sorkina et al, CA 56-14888 (1962).
Sorkina, CA 61-8783 (1964).
Lentia G.m.b.H, CA 62-6494 (1965).
Zikolova et al, CA 70-115123e (1969).
Shetty et al, CA 92-128854y (1980).
Wunderlich, CA 72-79097e (1970).
Kon et al, (1950), *Journal of the Chemical Society*, "Some Compounds Related to the Aromatic Nitrogen Mustards", 1:978-982.
Burchenal et al, (1951), *Cancer*, "Chemotherapy of Leukemia", 4:353-356.
Ishidate et al, (1961), *Chemical and Pharmaceutical Bulletin*, "Studies on Carcinostatic Substances, XXXVIII, Chemical and Antitumor Properties of Monofunctional . . . 9:996-999.
Sakurai et al, (1961), *Cancer Chemotherapy Reports*, "Antitumor Activity of Derivative of Nitrogen Mustard Containing a 2-Chlorethyl Group", 13:205-210.

*Primary Examiner*—Donald G. Daus
*Assistant Examiner*—Cecilia Shen
*Attorney, Agent, or Firm*—Holman & Stern

[57] ABSTRACT

New nitrogen mustard analogs with arms of unequal reactivity on different nitrogen atoms have been made. The new analogs are less toxic, potent, cancer chemotherapentic agents.

2 Claims, No Drawings

CHEMOTHERAPEUTIC 1-(2-CHLOROETHYL)-4-(3-CHLOROPROPYL)-PIPERAZINE, DIHYDROCHLORIDE

BACKGROUND OF THE INVENTION

1. Technical Field

The present invention is related to nitrogen mustard analogs with arms of unequal reactivity on different nitrogen atoms. More particularly, the present invention is related to 1-(2-chloroethyl)-4-(3-chloropropyl)-piperazine, dihydrochloride or similar halo-derivatives and method of preparing the same. The new analogs are less toxic, potent, cancer chemotherapeutic agents.

2. State of the Art

Tertiary amine alkylating agents with one or two beta-haloethyl groups attached to nitrogen have been used in a variety of pharmacologic regimens. The former are employed principally as alpha adrenergic blockers and the latter, frequently described as nitrogen mustards, are cytotoxic agents. Analogs of nitrogen mustards containing a beta-haloethyl group and a gamm-halopropyl group attached to the same nitrogen have been known and reported to be effected cancer chemotherapeutic agents. Piperazine mustard, 1,4-bis(2-chloroethyl)piperazine, has also been prepared and found to be active against murine leukemia (Burchenal et al., Cancer, 4: 353, 1951), but its analog containing a beta-chloroethyl group and a gamma-chloropropyl group on different nitrogens has not been produced.

SUMMARY OF INVENTION

It is, therefore, an object of the present invention to provide new analogs of nitrogen mustard with arms of unequal reactivity on different nitrogen atoms.

It is a further object of the present invention to provide new analogs of nitrogen mustard with decreased host toxicity (LD50) but with equal or greater chemotherapeutic activity compared to mechlorethamine.

Other objects and advantages will become evident as the detailed description of the present invention proceeds.

DETAILED DESCRIPTION OF INVENTION

The above and various other objects and advantages of the present invention are achieved by new analogs of nitrogen mustard with arms of unequal reactivity on different nitrogen atoms, a preferred analog being 1-(2-chloroethyl)-4-(3-chloropropyl)-piperazine, dihydrochloride.

Unless defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

EXAMPLE 1

Preparation of 1-(2-chloroethyl)-4-(3-chloropropyl)piperazine, dihydrochloride

Preparation of 1-(2-hydroxyethyl)-4-(3-hydroxypropy)-piperazine [I]:

1-(2-hydroxyethyl)-piperazine, 26 grams, freshly distilled allyl alcohol, 36 g and sodium hydroxide, 8 g are heated to 118°–120° C. for 36 hours. The viscous reaction mixture is taken up into 250 ml water, and solid potassium carbonate is added to saturate the warmed solution. A yellow oil, the product, rises to the top. It is extracted with tetrahydrofuran, the solvent evaporated, the residue dissolved in ethanol, the solution filtered, and the ethanol evaporated under vacuum to a thick oil, which solidifies on standing to give the isolated product, [I], above.

EXAMPLE 2

Preparation of 1-(2-chloroethyl)-4-(3-chloropropyl)piperazine, dihydrochloride [II]:

The dihydroxy compound, [I], 10 g, described above, is dissolved in 100 ml dimethylformamide and the solution is cooled in an ice-bath. To the solution is added carbon tetrachloride (25 ml) and triphenylphosphine (28 g) and the mixture stirred for four hours at room temperature (22°–25° C.). The solution is evaporated under vacuum and the residue taken up in 2N hydrochloric acid. The precipitate, triphenylphosphine oxide, is removed by filtration and the clear solution brought to pH 8 with 2N sodium hydroxide. It is extracted 3 times with ethyl acetate, dried with anhydrous sodium sulfate and the solvent removed by evaporation in vacuo. The oil obtained is dissolved in a minimal volume of ethyl acetate and the solution mixed with hydrochloric acid in dioxane to precipitate a white solid, the product, (II).

Of course, the amounts shown in the above examples are only illustrative. Upgrading and adjustment of various parameters described in the above methods for large scale production can be easily achieved by one of ordinary skill in the art to which the present invention belongs.

Animal studies

Male CDF$_1$ mice (Balb/c×DBA/2), 8–12 weeks old and weighing 22–31 grams, were placed in groups of equivalent weight, 5 or 6 animals per plastic cage with wood chip bedding and were given laboratory chow ad libitum. L1210 cells of the NCI strain were maintained in female DBA/2 mice and transplanted intraperitoneally (i.p.) into male CDF mice for experiments. They were harvested on day seven following the inoculation of 1×10$^5$ cells.

Chemotherapy of L1210 leukemia bearing mice

The most effective treatment schedule for mice with 1-(2-chloroethyl)-4-(3-chloropropyl)piperazine was obtained by daily intraperitoneal injections, which resulted in an increase in survival of 67% over controls (Table 1). Increased survival with the standard nitrogen mustard, mechlorethamine, was only 61%.

TABLE 1

Treatment of Mice Bearing L1210 Leukemia with
1-(2-Chloroethyl)-4-(3-Chloropropyl)piperazine 2HCl
L1210 cells, 1 × 10$^5$, were injected i.p. on day 0
and treatment was begun i.p. on day 1.
There were 6 mice per group.
T/C is survival in days of treated animals
divided by survival of controls.

| Treatment (mg/kg) | Mean Survival Time (days) | T/C (%) |
| --- | --- | --- |
| 0 | 8.2 | 100 |
| 100 (day 1) | 7.0 | 85* |
| 50 (day 1) | 11.4 | 139 |
| 25 (day 1) | 10.0 | 122 |
| 10 (days 1–5) | 11.5 | 140 |
| 5 (days 1–5) | 9.8 | 120 |

TABLE 1-continued

Treatment of Mice Bearing L1210 Leukemia with
1-(2-Chloroethyl)-4-(3-Chloropropyl)piperazine 2HCl
L1210 cells, $1 \times 10^5$, were injected i.p. on day 0
and treatment was begun i.p. on day 1.
There were 6 mice per group.
T/C is survival in days of treated animals
divided by survival of controls.

| Treatment (mg/kg) | Mean Survival Time (days) | T/C (%) |
|---|---|---|
| 2.5 (days 1-5) | 9.2 | 112 |
| 1.25 (days 1-5) | 8.8 | 107 |
| 0 | 8.2 | 100 |
| 30 (days 1-5) | 8.0 | 98* |
| 20 (days 1-6) | 12.0 | 146 |
| 10 (days 1-7, 10) | 13.7 | 167 |
| 0 | 8.0 | 100 |
| 10 (days 1-5) | 12.6 | 158 |

*T/C less than 100% is due to toxicity.

Chemotherapy against a spectrum of tumors:

Tables 2 and 3 show a drug screening summary of NSC 344007 (the compound of the present invention). It can be seen that the compound is surprisingly effective in the human tumor colony forming assay, against a number of murine tumors and in a human tumor xenograft test.

TABLE 2

HUMAN TUMOR COLONY FORMING ASSAY
CONFIRMATION TESTING
(DOSE RESPONSE)

| TUMOR GROUP | EVALUABLE/TOTAL ASSAYS | RESPONSES | TUMOR GROUP | MODR |
|---|---|---|---|---|
| MELANOMA | 5/5 | 4 (80%) | MEL | |
| OVARIAN CARCINOMA | 4/4 | 1 (25%) | OVA | |
| TOTAL | 9/9 | 5 (55%) | ALL GROUPS | |
| OVERALL RESPONSE RATE AT 10 OR LESS MCG/ML | 5/9 | (55%) | | |

AN OVERALL RESPONSE RATE OF 20% OR GREATER IS THE CURRENT ACCEPTABLE GUIDELINE.

colon 38 carcinoma, the cis-platin and L-PAM resistant P388 leukemias. It gave reproducible cures for the B16 melanoma and the M5076 sarcoma and was highly active (++) in the human mammary subrenal capsule xenograft (MX-1) and scored positive in 4 of 5 tests in the human melanoma colony forming assay (Tables 2 and 3). The results indicate that the compound of the present invention has both carcinocidal as well as carcinostatic properties.

Of course, the compounds of the present invention can be used in a pharmaceutical composition comprising a chemotherapeutically effective amount of the compound in a pharmaceutically acceptable carrier such as sterile water, physiological saline, non-toxic physiological fillers and/or buffers and the like well known in the art. The composition can be in any suitable form such as a liquid, a solid, a capsule, a tablet, a paste or creamy mixture and the like.

It is understood that the examples and embodiments described herein are for illustrative purposes only and that various modifications or changes in light thereof will be suggested to persons skilled in the art and are to be included within the spirit and purview of this application and the scope of the appended claims.

I claim:

TABLE 3

| SYSTEM | NAME OF TUMOR | RATING ++/+/- | RT | SCHEDULE | T/C | OD MG/KG | CURES/TOT |
|---|---|---|---|---|---|---|---|
| 3B131 | B16 MELANOMA | ++ | IP | QD1-9 | 260 | 10 | 3/10 |
| 3LE31 | L1210 LEUKEMIA | ++ | IP | QD1-9 | 209 | 10 | 0/10 |
| 3MBG5 | HUMAN MAMMARY TUMOR IN SUBRENAL CAPSULE | ++ | SC | Q4DX3 | −61 | 15 | 2/6 |
| 3M531 | M5076 SARCOMA | ++ | IP | Q4DX4 | 240 | 20 | 5/10 |
| 3PS31 | P388 LEUKEMIA | ++ | IP | QD1-5 | 238 | 10 | 0/5 |
| 3PO31 | CYTOXAN RESISTANT P388 LEUKEMIA | ++ | IP | QD1-5 | 197 | 9 | 0/10 |
| 3C872 | COLON 38 CARCINOMA | + | IP | Q7DX2 | 16 | 20 | 0/10 |
| 3CDJ2 | CD8F₁ MAMMARY TUMOR | ++ | IP | Q1DX1 | −43 | 40 | 0/10 |
| 3LE32 | L1210 LEUKEMIA | + | IP | QD1-9 | 138 | 10 | 0/10 |
| 3CP31 | CIS PLATIN RESISTANT P388 LEUKEMIA | + | IP | QD1-5 | 170 | 13 | 0/10 |

In summary, the compound of the present invention when tested according to the protocols of the Development Therapeutics Program, Division of Cancer Treatment, National Cancer Institute, is found to be highly active (++) against the following mouse tumors: the B16 melanoma, the CD8F1 mammary adenocarcinoma, the P388 and L1210 leukemias, the M5076 sarcoma, the cytoxan resistant P388 leukemia and active (+) in the 1. 1-(2-chloroethyl)-4-(3-chloropropyl)-piperazine, dihydrochloride.

2. A pharmaceutical composition comprising a chemotherapeutically effective amount of 1-(2-chloroethyl)-4-(3-chloropropyl)-piperazine, dihydrochloride to inhibit growth of tumors and a pharmaceutically acceptable carrier.

* * * * *